United States Patent [19]

Miller, Jr. et al.

[11] Patent Number: 5,249,929
[45] Date of Patent: Oct. 5, 1993

[54] LIQUID CHROMATOGRAPHIC PUMP

[75] Inventors: Theodore E. Miller, Jr.; Charles M. Davis, both of Midland, Mich.

[73] Assignee: The Dow Chemical Company, Midland, Mich.

[21] Appl. No.: 566,931

[22] Filed: Aug. 13, 1990

Related U.S. Application Data

[63] Continuation of Ser. No. 393,431, Aug. 11, 1989, abandoned.

[51] Int. Cl.$^5$ .................................................. F04B 19/24
[52] U.S. Cl. .................................... 417/207; 417/379; 417/395; 222/146.5
[58] Field of Search ................ 417/20, 43, 52, 207, 417/208, 209, 379, 395; 210/198.2, 101; 222/146.2, 146.5

[56] References Cited

U.S. PATENT DOCUMENTS

| | | | |
|---|---|---|---|
| 1,973,541 | 10/1934 | Proctor | 417/52 |
| 3,586,461 | 6/1971 | Erlandson | 417/379 |
| 3,827,675 | 8/1974 | Schuman | 417/207 |
| 3,898,017 | 8/1975 | Mandroian | 417/209 |
| 4,265,601 | 5/1981 | Mandroian | 417/379 |
| 4,300,075 | 11/1981 | Foose et al. | 315/307 |
| 4,392,791 | 7/1983 | Mandroian | 417/379 |
| 4,775,481 | 10/1988 | Allington | 417/43 |

Primary Examiner—Richard A. Bertsch
Assistant Examiner—Michael I. Kocharov

[57] ABSTRACT

A liquid chromatographic method and apparatus is disclosed which employs an improved pump not requiring driven pistons or sliding seals. The pump comprises at least one length of tubing forming a chamber disposed between first and second check valves, controllable heating means to periodically heat liquid in said chamber effective to pump relatively low volumes of liquid from the chamber at relatively high pressures, means for measuring the pressure developed by the pump, and control means to increase and decrease the amount of heat imparted to the liquid to maintain the pump operation at a controlled pressure setpoint.

14 Claims, 7 Drawing Sheets

_Fig. 7_

_Fig. 5_

_Fig. 6_

LIQUID CHROMATOGRAPHIC PUMP

CROSS-REFERENCE TO RELATED APPLICATION

This is a continuation of application Ser. No. 393,431, filed Aug. 11, 1989, abandoned.

FIELD OF THE INVENTION

This invention relates to an improved pump particularly suited for use in liquid chromatographic applications. More particularly, this invention relates to an improved pump having no positively driven parts in its drive mechanism, relying upon thermal expansion principles, which is nevertheless capable of supplying fluid at the extremely high pressures required for liquid chromatographic and other experimental and analytical uses.

BACKGROUND OF THE INVENTION

In recent years, liquid chromatography, including in this term a wide variety of experimental and analytical techniques, has become by far the preferred technique for laboratory analysis of the properties of polymers. Stated generally, the principles of liquid chromatography involve the supplying of a liquid sample (for example, of polymer in solution) to a separation column containing a separation medium at very high pressure. Over time, a sample stream elutes from the column, the constituents of which vary during elution as a function of the properties of the material being analyzed and of the separation medium. As mentioned, a wide variety of different liquid chromatographic techniques are known and will not further be discussed here.

As mentioned, substantially all liquid chromatographic techniques involve the supply of a sample fluid to a separation column at high pressure, typically on the order of 500 to 5,000 psig. Accordingly, a high pressure pump is required. As a rule, the pumps used in liquid chromatography are mechanically-driven piston pumps of one type or another, all of which have certain unavoidable defects. More particularly, all piston pumps require a seal between a piston or the equivalent and a cylinder or the equivalent. These seals are subject to wear over time and accordingly maintenance must be performed from time to time. Another significant defect of piston pumps is that they are extremely expensive. One pump which may be considered generally representative of the state of the art at the time of filing of this application costs a minimum of $4,000 and even then requires modification in many circumstances. Variation of the flow rate of prior art piston pumps typically requires adjustment of a mechanical linkage, which also is subject to wear over time; therefore, such pumps require periodic calibration if flow rates are to be kept more or less constant.

Many if not most liquid chromatographic techniques are desirably implemented by supplying sample to the column in increments of constant volume, that is, at a constant flow rate. The provision of equal-volume samples to the separation column is difficult with ordinary piston pumps, because the volume of sample pumped for a given piston stroke can vary with varying conditions in the pump (for example, temperature and seal wear) and in the column (for example, clogging) over time. It would be desirable to provide volume-related automatic feedback control signals to the pump from an accurate flowmeter disposed downstream of the pump, so as to be able to provide substantially constant flow, that is constant increments of volume per unit time. As mentioned above, however, adjustment of the flow rate provided by mechanical pumps frequently involves adjustment of a mechanical linkage, which can be difficult to perform automatically, such that control based on feedback of a flow rate signal is sometimes awkward to implement. Furthermore, mechanical linkages of some types only provide flow rate adjustment in finite increments, so that the exact flow rate desired may not be available. Therefore, a high pressure pump suited to automatic flow rate control by means of feedback and being operable to provide substantially any desired flow rate is needed by the art.

Another deficiency of conventional piston pumps as used in liquid chromatography is that their output inherently includes pressure pulses, which appear as noise in the output signal provided by the liquid chromatographic apparatus. A wide variety of pressure damping techniques and devices are known, none of which are entirely satisfactory and all of which necessarily involve some additional complication. It would therefore be desirable to provide a pump which at least offers the possibility of improved continuity of flow.

These problems are generally recognized in the art. See, for example, Abrahams et al. U.S. Pat. No. 3,855,129 which purports to address and solve some of the problems existing with prior art piston pumps. The Abrahams et al device is, however, an improved piston pump, and would appear likely to suffer from many of the deficiencies noted.

In addition to piston pumps, the prior art also teaches what may be termed "thermal pumps." Speaking generally a thermal pump comprises a fluid chamber in series with first and second check valves on its inlet and outlet sides. Heat is supplied to the chamber, causing the fluid in it to expand, possibly undergoing a partial change of phase, and forcing a portion of the fluid past the outlet check valve. Upon cessation of application of heat, the fluid in the chamber contracts, causing additional fluid to be drawn past the inlet check valve. The process is then repeated.

Proctor U.S. Pat. No. 1,973,541 shows a thermal pump for use in a deep oil well, in which these general principles are employed. See also Hutton U.S. Pat. No. 1,630,943 also generally showing a pump of this type, and disclosing that it may be useful in connection with "certain fluid testing devices and the like". However, both the Proctor and the Hutton pumps have significant defects which would render them useless in the modern liquid chromatographic environment. For example, neither seems suitable for generating the very high pressures required. Nor does either appear to show any means by which a relatively sophisticated feedback control could be incorporated in order to provide a relatively continuous flow rate. Hutton in particular shows a relatively crude thermostatic control arrangement which would seem quite unsuited to a laboratory environment.

See also Brown U.S. Pat. No. 3,819,299, which shows a "magnetocaloric pump" in which a fluid is caused to expand by being heated The heating is accomplished by applying a magnetic field to a magnetocaloric material, that is, one which is heated when subjected to a magnetic field, the material being in thermal contact with the fluid to be pumped. Brown provides only timers for control.

Bowen et al. U.S. Pat. No. 3,195,806 shows a pump for high pressure pumping of gases. Bowen et al. teach a pump comprising a lengthy capillary of electrically resistive material disposed between first and second check valves. A current is passed through the capillary, heating its contents and causing them to expand, thus being pumped through the outlet check valve. Bowen et al. do not teach a control system other than a power switch.

A further document showing pumping of liquid by heating thereof in a chamber disposed between inlet and outlet check valves is Van Hise U.S. Pat. No. 1,686,887. van Hise also shows a power switch as the only control element.

Mandroian U.S. Pat. No. 4,265,600 describes a diaphragm-type thermal pump, in which the fluid to be pumped; is separated by a flexible diaphragm from a pumping fluid. The pumping fluid is heated by passing an electric current through a resistive filament disposed in a chamber containing the pumping fluid. The pumping fluid is a volatile liquid or gas, such that when heated it expands, forcing the diaphragm into a second chamber filled with the fluid to be pumped. The second chamber is connected by check valves to a source and sink of fluid, e.g. a container of saline solution, and a patient, respectively.

Mandroian teaches feedback of flow rate and/or pressure signals for control of supply of current to the heating element, and teaches that use of the diaphragm arrangement simplifies preservation of the sterility of the pumped fluid. The Mandroian pump does not appear suitable for liquid chromatographic applications, as it is apparently limited to very low pressures. Note the embodiment of FIG. 3, which the pumping fluid chamber is vented to the atmosphere. Further it would appear that Mandroian is limited to pulsatile flow; see col. 4, lines 38-54. As mentioned above this is frequently undesirable.

Accordingly, a need exists in the art for an improved pump suitable for use in liquid chromatographic and other high-pressure, low flow rate applications.

OBJECTS OF THE INVENTION

It is therefore an object of the invention to provide an improved pump for liquid chromatography which does not involve driven pistons or sliding seals.

It is a further object of the invention to provide an improved pump suitable for liquid chromatography in which pressure and flow rate are variable over wide ranges and in any desired increment, while not requiring adjustment of mechanical linkages or the like.

It is a further object of the invention to provide an improved pumping system suitable for use in liquid chromatographic applications in which feedback of flow rate and/or pressure can be automatically utilized to control the pump.

It is a further object of the invention to provide an improved liquid chromatographic pumping system comprising an inexpensive pump and an improved flowmeter, such that setup is simple and foolproof, and according to which feedback-controlled, continuously variable flow rates are provided.

It is a further object of the invention to provide a pump suitable for use in liquid chromatographic applications which is of lower cost than piston pumps presently available.

It is an object of the invention to provide a pump suitable for use in liquid chromatographic applications which is of substantially improved utility in such applications than are pumps now presently available.

SUMMARY OF THE INVENTION

The invention achieves the needs of the art and objects of the invention mentioned above by provision of an improved "electrothermal" pump. The pump comprises in a first preferred embodiment a length of stainless steel capillary tubing in series between first and second check valves. This assembly is filled with the fluid to be pumped. An electric current is passed through the coil, raising the temperature of the liquid therein substantially. Accordingly, the liquid expands and/or undergoes at least a partial change of phase, and is forced through the check valve on the outlet end of the tubing. Liquid is prevented from being forced out of its inlet end by the check valve on its inlet side. After a period of time, the electric current is removed, allowing the coil and the liquid therein to cool. A partial vacuum is then created, and the tubing is refilled from a supply of the liquid to be pumped through the check valve located on the inlet side. The cycle may then be repeated. Variation in the flow rate and/or pressure is accomplished by variation of the amount of power supplied to the coil, either by varying the amplitude of a current signal supplied thereto, or by varying the duty cycle of application of the current. Power control may be effected by way of any of a number of expedients, and is readily adaptable to feedback control responsive to a flow rate signal.

In a further preferred embodiment of the invention, plural lengths of tubing, formed into coils for compactness, and each plumbed in series with inlet and outlet check valves are provided The "cool off" periods of their operation are staggered, and their inlets and outlets are joined at common fittings, such that liquid at elevated pressure is continuously available to experimental apparatus connected to their common outlet.

In an additional preferred embodiment of the invention, the pumped fluid is prevented from being heated. The pumped fluid is supplied to a chamber, one wall of which is formed by a flexible diaphragm. Check valves are plumbed to the inlet and outlet sides of the chamber. A working fluid, elevated in pressure by heating, is supplied to the other side of the diaphragm, deflecting it and causing the pumped fluid to be forced past the outlet check valve. Plural diaphragm assemblies and coils for heating the working fluid may be employed in a further preferred implementation of this embodiment of the invention.

Finally, in an ultimately preferred embodiment of the invention, it comprises a complete system for liquid chromatographic analysis including the electrothermal pump of the invention, an improved time-of-flight flow meter which provides an output signal suitable for feedback to the pump of the invention, a liquid chromatographic separation column and a controller device. This pumping system provides ready and accurate control of the rate of flow of the pumped fluid though the column, for improved analytical capability.

BRIEF DESCRIPTION OF THE DRAWINGS

The invention will be better understood if reference is made to the accompanying drawings, in which:

FIG. 9($a$-$g$) show timing diagram illustrating operation of the power supply circuitry of the pump of the invention.

DESCRIPTION OF THE PREFERRED EMBODIMENTS

As discussed in detail above, modern liquid chromatography requires high pressure pumps to deliver fluid samples in solution to separation columns at high pressures (500–5,000 psig) and low flow rates (0.1–5 cc/min). Piston pumps are near universal in these applications, but have numerous disadvantages, most notably the wear of the piston seal sliding within the cylinder, the difficulty of adjustment of the stroke in response to the changes in flow rate and/or pressure, noise in the output pressure, and cost.

The thermal pumps available in the prior art do not solve these problems. An improved pump suitable for the substantially continuous supply of fluid at high pressures, suitable for liquid chromatography and other similarly demanding applications continues to be required.

Figure 1:
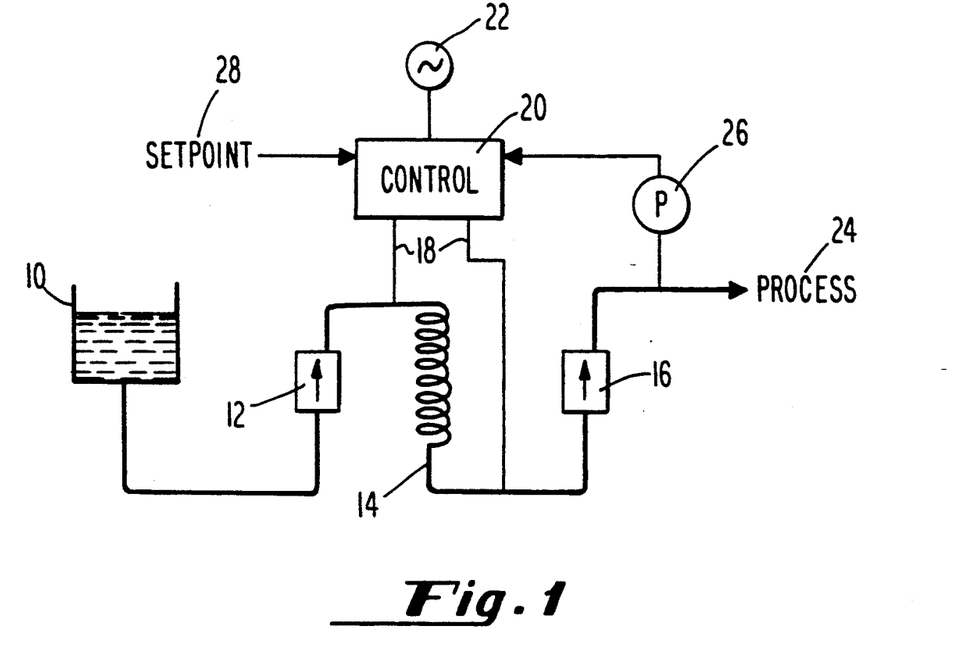
FIG. 1 shows a schematic view of the apparatus of the pump of the invention in a first embodiment.

FIG. 1 shows the pump of the invention in schematic view. A fluid to be pumped is supplied from a reservoir 10 to a first check valve 12, which permits flow only in the direction of the arrow. The fluid fills a coil of tubing 14, the outlet of which is connected to a second check valve 16, which again permits flow only in the direction of the arrow shown. Electrical power is supplied to both ends of the coil 14 by leads 18 connected to a controller 20, which comprises means for switching a power source 22 into circuit with the coil of tubing 14. Upon placing the power supply 22 into circuit with the coil 14, the fluid within the coil 14 is heated, causing it to expand, and possibly to enter the gaseous phase to some degree. The fluid is thus forced past the outlet check valve 16, to be supplied a point of use of the fluid, such as a liquid chromatographic or other process, as indicated generally at 24.

The outlet pressure is monitored by a suitable transducer 26 and may be compared by controller 20 with a setpoint, as indicated generally at 28. In the preferred embodiment, power is supplied at a steady rate, determined by comparison of the pressure signal to the setpoint, for a predetermined length of time. At the end of this period, the supply of power is shut off, causing flow to stop. Check valve 16 thereupon closes. When the fluid within the coil 14 subsequently cools, a partial vacuum is created in the coil 14, causing further fluid to be drawn through check valve 12 from the reservoir 10, preparing the pump for a second cycle.

It will be appreciated that as thus described, control of the pump of the invention involves feedback provided directly to a heating element. Note further that the wall of the tubing forming the coil 14 is itself the electrical resistance element which heats the fluid therewithin; this provides extremely direct coupling of the thermal energy to the fluid, which results in fast pump response. The relatively high surface to volume ratio of the tubing, which is a stainless steel capillary, also provides relatively fast cooling upon cessation of supply of power thereto, which is highly significant in instantaneous pressure regulation.

Figure 2:
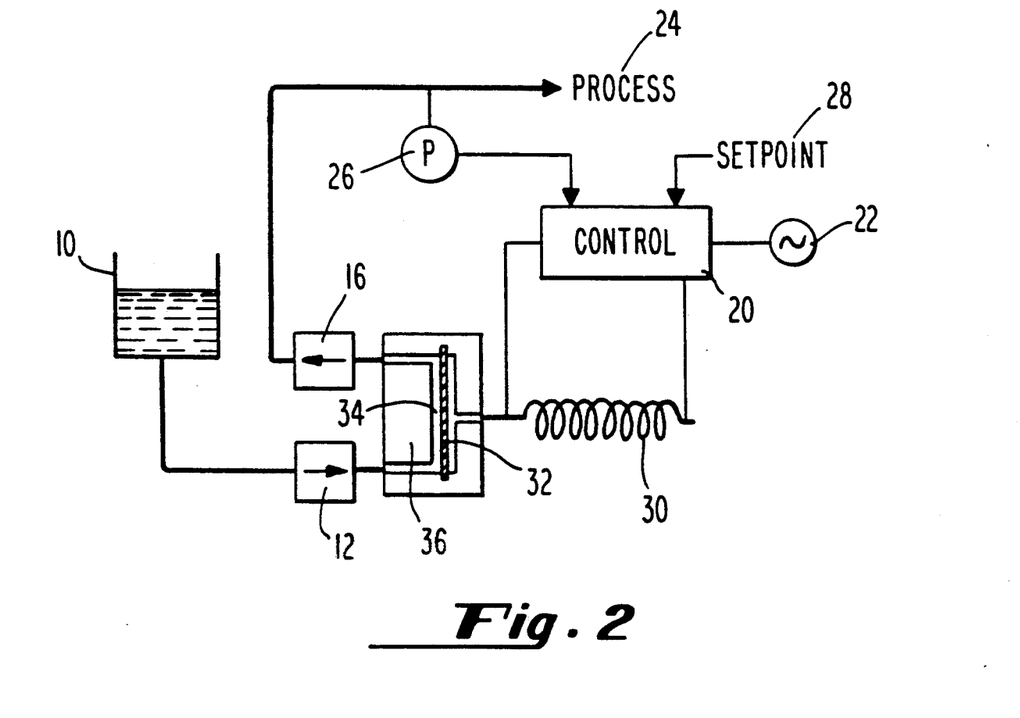
FIG. 2 shows a schematic diagram comparable to FIG. 1 of the pump of the invention in a second embodiment.

It will be appreciated by those skilled in the art that the fluid to be pumped is heated by the pump of FIG. 1. In some cases this may be a disadvantage. Furthermore, some liquids to be pumped may not expand sufficiently upon heating to be pumped successfully. FIG. 2 shows a second embodiment of the invention in which these drawbacks and limitations of the embodiment of FIG. 1 are avoided.

FIG. 2 shows as mentioned a second embodiment of the invention in which heating of the fluid to be pumped from a reservoir 10 to a process 24 is to be avoided, and in which substantially any fluid can be pumped. As in the embodiment of FIG. 1, liquid passes from a reservoir 10 through first and second check valves 12 and 16. Again the pressure is monitored at 26 and compared to a setpoint input at 28 by a controller 20 controlling the supply of power from source 22. However, in this case the power is not applied to a coil of tubing containing the fluid to be pumped, but is applied to a separate coil 30 which is filled with a fixed amount of a working fluid, such as water. When current is supplied to the coil 30, the fluid therein is heated and expands, causing a diaphragm 32 in a diaphragm cell 36 (discussed in detail below in connection with FIG. 5) to expand into a cavity 34 containing the fluid to be pumped. The fluid to be pumped is then urged past check valve 16.

When the fluid in the coil 30 is thereafter cooled, by cessation of supply of electrical power thereto, the diaphragm 32 is permitted to return to its original position. A partial vacuum is then formed between check valves 12 and 16, drawing additional fluid past check valve 12 into the cavity 34 for subsequent pumping. As mentioned, controller 20 is provided with a setpoint 28, which it compares to the pressure signal from transducer 26, in order to determine the amount of power to be supplied from source 22 to the coil 30. In this way the pressure of the fluid supplied to process 24 is accurately controlled through use of feedback.

Those skilled in the art will recognize that according to both of the embodiments of the invention shown in FIGS. 1 and 2, fluid is pumped periodically; that is, flow to the process 24 is halted while the coil is permitted to cool and the fluid volume between the check valves refills. In some cases this may be a disadvantage, and steady flow may be preferred. In further preferred embodiments of the invention, corresponding to the embodiments of FIGS. 1 and 2, dual coils and paired check valves are provided, and the sequence of their operation is arranged such that at least one pump is continually pumping fluid, such that relatively steady flow is provided.

Figure 3:
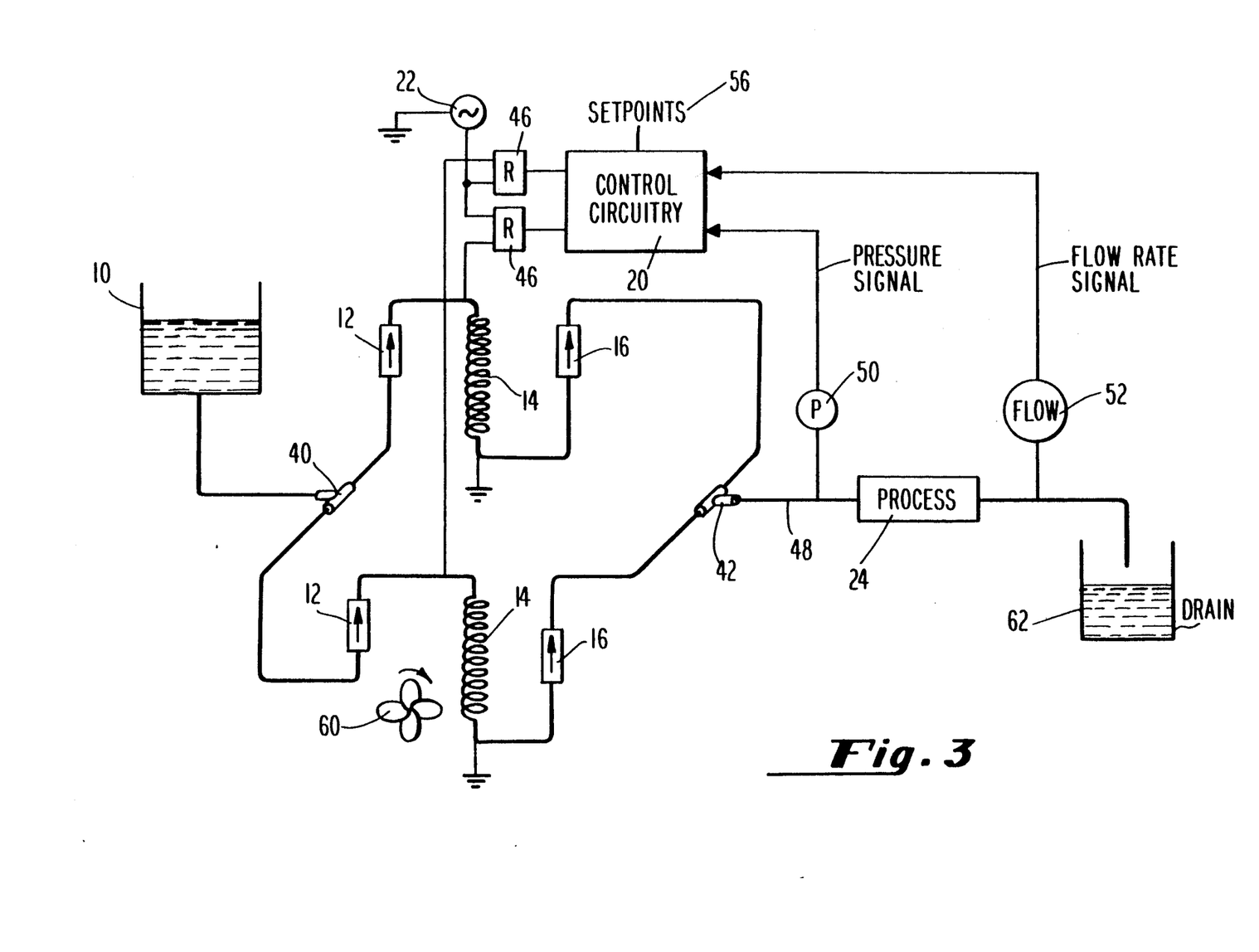
FIG. 3 shows a complete pumping system in accordance with the principles of the invention in the first embodiment.
Figure 4:
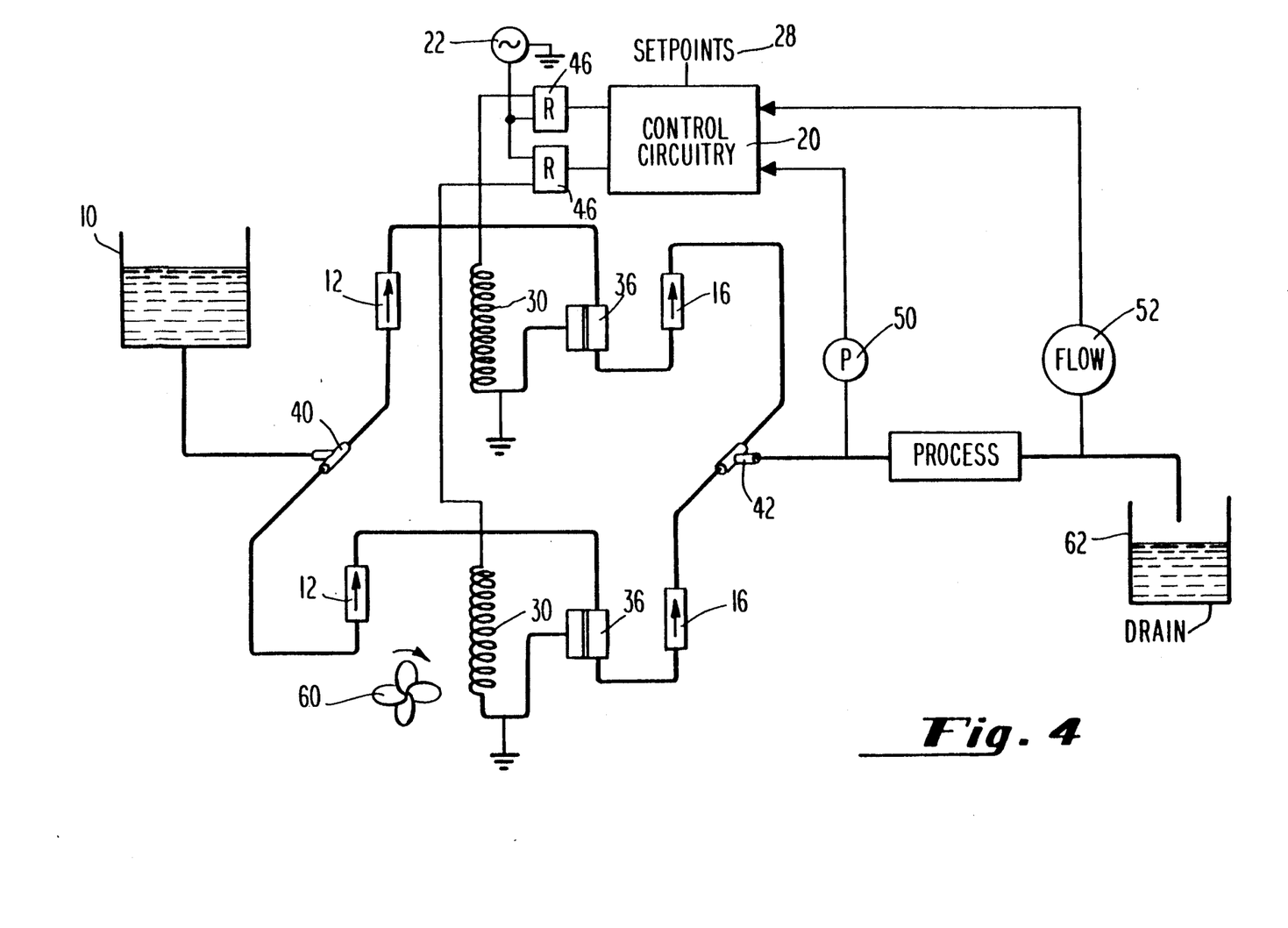
FIG. 4 shows a complete pumping system in accordance with the principles of the invention in the second embodiment.

FIGS. 3 and 4 show diagrams corresponding to the embodiments of FIGS. 1 and 2 in which such plural coil/check valve combinations are provided. Certain details of the preferred implementation of the invention are also discussed in connection with these figures.

FIG. 3 shows a multicoil realization of the embodiment of the invention shown in FIG. 1. The fluid to be pumped is supplied from a reservoir 10 by way of a tee fitting 40 to plural check valves 12. Check valves 12 are connected to plural coils 14, which then are connected to outlet check valves 16. Flow therefrom is to a second tee fitting 42, and thence to process 24. One end of each of the coils 14 is connected to one of two relays 46 which are controlled by control circuitry 20. Relays 46 control supply of power from source 22 to coils 14. The other ends of the coils 14 are grounded, as indicated, to complete the electrical circuit. Pressure in the outlet line 48 is monitored at 50 and a pressure signal is supplied to the control circuitry.

Upon elution of the fluid to be pumped from the process 24, its flow rate is monitored by a transducer 52; after exiting the flow meter 52 the fluid may be sent to a drain 62. In the preferred embodiment transducer 52 is a thermal pulse time-of-flight flow meter as described in commonly assigned U.S. Pat. No. 4,491,024. This device is sold as a "Thermal Pulse Liquid Flowmeter" by Molytek, Inc., Pittsburgh, Pa. Flow meter 52 comprises a tube having first and second thermistors in communication with a fluid flowing therein. A first upstream thermistor is supplied with a pulse of current and imparts a thermal pulse to a flowing sample. A second thermistor disposed downstream detects passage of the sample bearing the thermal pulse. The rate of flow of the liquid may be determined by measurement of the time lag between input and detection of the pulse.

The flow rate signal from flow meter 52 is supplied to the control circuitry 20, as is the pressure signal; these may both be compared to setpoints, indicated generally at 56, for feedback control cf supply of power to the coils 14, resulting in control of the flow rate and flow pressure.

In the preferred embodiment the coils 14 are formed of 0.040" ID, 1/16" OD stainless steel tubing. Typically each coil is formed of approximately 80 inches of the tubing, for a total fluid capacity on the order of 2 cc. Such a coil has an electrical resistance of approximately 2 ohms. Applicants find that application of 300 watts to such a coil, filled with a fluid of specific heat generally similar to that of water, for a period of approximately 45 seconds, will result in pumping of the fluid at approximately 500 psi outlet pressure at a flow rate of on the order of 1 cc per minute. Such a cycle yields a mixture of gas and liquid phases at the end of the heating cycle.

It will be apparent to those skilled in the art that the overall response of the pump of the invention varies in part on the function of the check valves 12 and 16. In the preferred embodiment of the invention, model 02-0129 check valves from Alltech Corp., of Deerfield, Ill., which open in response to an 0.3 psi pressure differential, are used. These check valves comprise O-ring seals carried by members sliding within recesses under their own weight. The seal is made between an end of the recess within which the member slides and the surface of the O-ring juxtaposed thereto. In this way, the outer peripheral surface of the O-ring need not form a sliding seal with the wall of the recess. The problems posed by sliding seals in high-pressure systems, particularly encountered in mechanical pumps, are thus largely avoided in favor of a simple, gravity actuated, face-to-face seal. It should be appreciated, nonetheless, that other sorts of valves, including solenoid valves operated by the controller 20, are within the scope of the invention; their implementation is considered to be within the skill of the art.

A final element of the system shown in FIG. 3 is a fan 60 which is used to blow air over the coils 14, ensuring that they cool down quickly at the end of the heating cycle, to further increase maximum flow rate capability for a given coil size and current rating. It will be appreciated that the operation of the system of the invention does not require the capillary tubing to be in coil form; this expedient is adopted for compactness and convenience in cooling.

FIG. 4 shows a complete schematic diagram of the system of the invention in the second embodiment, that is, in which heating of the fluid to be pumped from reservoir 10 to process 24 is to be avoided. Flow of the fluid to be pumped is from reservoir 10, through tee fitting 40, first check valves 12, diaphragm units 36, second check valves 16, and second tee fitting 42, to process 24 and thence to a drain 62. The diaphragm units 36 couple presssure generated in a working fluid to the fluid to be pumped. The working fluid is contained by coils 30 and is heated by supply of electrical energy thereto. A fixed quantity of the working fluid within the coils 30, which may simply be water, may be confined between closed ends of the coils 30 and the diaphragms of the diaphragm units 36. The pumping cycle includes heating the water, forcing the diaphragms of the associated diaphragm units 35 to Pump the pumped fluid past check valves 16. The water must then cool sufficiently to recondense before subsequent heating cycles can be initiated.

In the embodiment of the invention shown in FIG. 4, the control circuitry 20 is again supplied with a pressure signal from a pressure transducer 50 and a flow rate signal from a flow meter 52, together with setpoint inputs 28. Using these, the control circuitry 20 can accurately determine the rate of supply of power from source 22 to coils 30. Control thus involves feedback A fan 60 is again provided to ensure rapid cooldown of the coils 30 and their contents during the "heat off" phase of operation.

Those of skill in the art will recognize that in the embodiment of the invention discussed in connection with FIGS. 1 and 3, efficient pumping requires expansion and/or at least a partial change of state of the fluid pumped. By comparison, the embodiment of the invention of FIGS. 2 and 4 is not so limited, and can pump substantially any fluid. The working fluid must be expansible or volatile, of course, but this is a trivial requirement; as indicated water is a fully satisfactory working fluid.

Figures 5, 7:
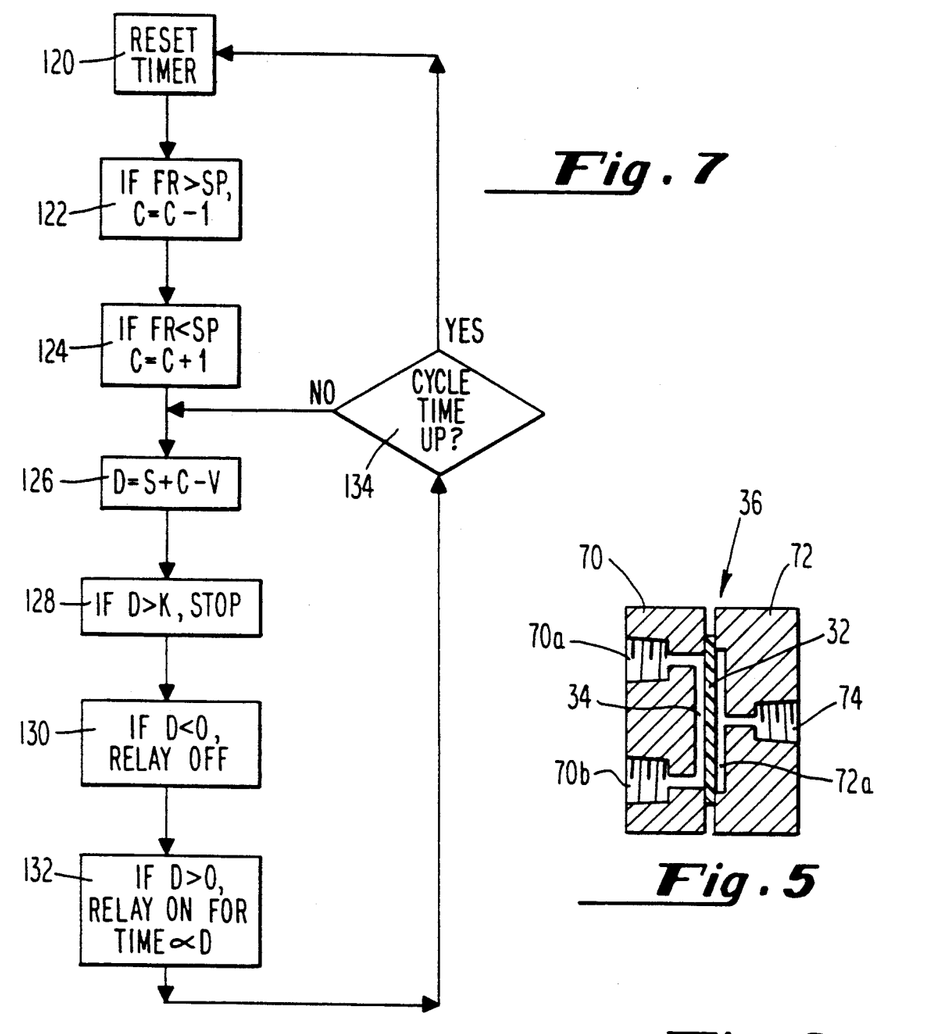
FIG. 5 shows a cross-sectional view of a diaphragm pumping cell useful in connection with the second embodiment of the invention.
FIG. 7 shows a flowchart of process steps taken by the controller in one particular embodiment of the invention.

FIG. 5 shows a schematic cross-sectional view of one of the diaphragm units 36 appearing in FIGS. 2 and 4. It comprises fist and second mating cell halves 70 and 72 which are held together by a number of bolts (now shown). A first inlet port 74 provides connection of the coil 30 for supply of pressurized liquid to a chamber 72a formed in cell half 72. Confined between the cell halves 70 and 72 is a diaphragm 32, which may be formed of Kalrez (trademark DuPont & Co.) or another flexible resilient material. The Kalrez diaphragm 32 separates the chamber 72a and a second chamber 34 which is in communication with inlet and outlet ports 70b and 70a respectively, which are in turn connected to check valves 12 and 16 (FIGS. 2 and 4). When pressurized fluid is supplied from coil (FIGS. 2 and 4) to the inlet port 74, the diaphragm 32 is flexed, leftwardly in FIG. 5, forcing fluid in chamber 34 out through outlet port 70a and check valve 16. When the diaphragm subsequently relaxes, a partial vacuum is created in chamber 34 which draws fluid in past check valve 12.

As mentioned briefly above, in both preferred embodiments of the invention, whether the system of FIG. 4 comprising the diaphragm unit of FIG. 5 or that shown in FIG. 3, in which the fluid to be pumped is itself heated in coils 14, two coils which are alternately heated and cooled are provided. In order that a relatively constant supply of fluid at constant pressure can be provided at the output, the duty cycle of the two coils is preferably such that at least one coil is "on", i.e. energized, at all times, while both are "on" at least about half the time. For example, each coil may be controlled to be "on" for approximately 46 seconds and then to be "off" for approximately 22 seconds. The "off" periods of the two coils are staggered from one another, to occur within the "on" periods of the other coil, such that 12 second periods during which both coils are "on" are separated by 22 second periods during which one of the coils is on.

This operational arrangement aids in providing a constant output pressure. For example, when a first coil is turned "on", the pressure it exerts at its corresponding outlet check valve 16 gradually builds up. Until the second coil turns "off", the pressure exerted by the second coil through tee fitting 42 on the seal of the first check valve 16 (i.e. that associated with the first coil), is greater than that exerted on the seal by the first coil. Therefore, the first check valve stays closed and there is no flow through it until power to the second coil is shut "off" and the fluid in it begins to cool. Only then can the first check valve 16 open, permitting flow from the first coil to begin. In this way, flow is maintained relatively constant, and the pressure signals from the transducer 50 show relatively little ripple or noise therein. This is in substantial contrast to many of the prior art mechanical pumps, which exhibit very significant noise which must be damped out, which while generally possible is frequently a nuisance.

The same generally smooth output pressure signal is observed in both embodiments of the invention, that is, with or without the diaphragm units 36. In both cases the pressure gradually builds up in the more recently turned "on" coil during the twelve-second period during which both coils are "on"; when the other coil is thereafter turned off, flow through the associated check valve 16 begins.

Figure 6:
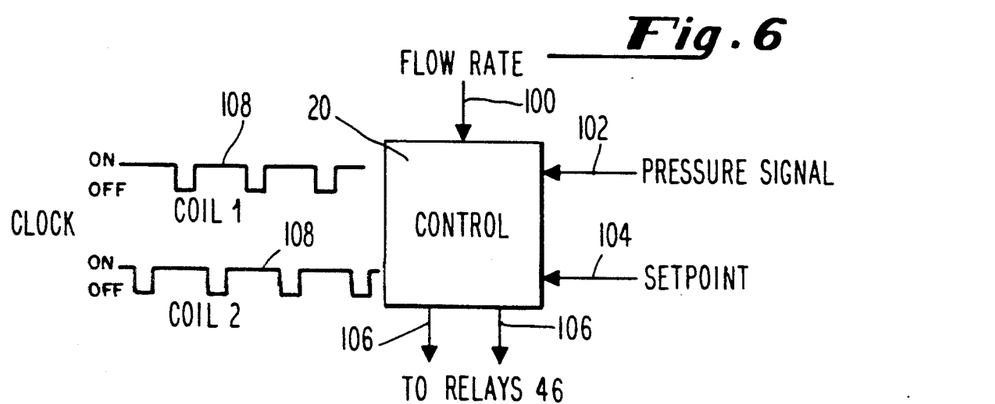
FIG. 6 shows in block diagram form one type of controller apparatus for controlling the pump of the invention.

FIG. 6 shows in schematic form the connections to the control circuitry 20 shown in the earlier figures. An external clock provides sequencing of the on/off signals 108 which establish the duty cycles of coils 1 and 2, which are further discussed below in connection with FIG. 9. The flow rate signal received from flow meter 52 (FIGS. 3 and 4) is input at 100 and indicates whether flow is equal to a setpoint, is too low, or is too high. Pressure signals 102 are received from transducer 50, for comparison to a setpoint signal 104 The outputs from controller 20 are control signals 106 used to control relays 46 (FIGS. 3 and 4). Relays 46 control the supply of power from a power supply 22 to the coils 14 (FIG. 3) and 30 (FIG. 4). These relays 46 can be any conveniently controllable solid state relays, a number of which are commercially available.

The method of this invention and the apparatus by which is practiced may be implemented using either analog, digital or hybrid technologies, depending, for example, on the nature of a data processing system controlling an experimental apparatus of which the pump of the invention is a part. In varying circumstances, each of these may be the preferred mode of practice of the invention. For example, the controller 20 of FIG. 6 may be equally conveniently implemented by a microprocessor or by "hard wired" logic circuitry.

FIG. 7 shows a flowchart of an exemplary microprocessor program, which might be used to control one of the solid state relays supplying electric power to one of the coils of the pump of the invention, in the embodiment of FIG. 3 or that of FIG. 4.

As mentioned above, typically each of the coils is turned on for a period of some 46 seconds and is then turned off for a period of some 22 seconds. As indicated at 120 of FIG. 7, a timer is reset at the beginning of the 46 second "on" period. At 122 the flow rate (FR) is compared to the setpoint for flow (SP); if the flow rate exceeds the setpoint, a quantity C is decremented by 1, as indicated. Similarly, if at 124 the flow rate is less than the setpoint for flow, the quantity C is incremented by 1. Thus, if the flow rate equals the setpoint, quantity C is unchanged. At 126, a quantity D, the power signal, is compared to the sum of S, the setpoint for pressure, plus the quantity C, indicative of flow rate with respect to setpoint, less the quantity V, which is the actual pressure. Thus if S, as adjusted by C, equals V, that is, if the pressure is equal to its setpoint, D is equal to 0, and no correction is needed.

In the example given, the value of D controls the amount of power supplied to the coil during the 46 second "on" period. This is detailed below. For fail-safe reasons, D is then compared at 128 to a number K which is set to a high value. If D>K, the entire process is stopped and an indication may be given that something is amiss with the instrument, since excessive power is being called for. If D is less than zero, indicating that the pressure is above its setpoint V, the relay is turned off at 130. If D is greater than zero, the relay is turned on for a time proportional to D, as indicated at 132.

Control is then returned to block 134; if this is the end of the 46-second "on" period for one of the coils, the "reset timer" block 120 is then reentered as described above. If not, the loop comprising blocks 126 through 134 is then reentered. This is performed repetitively, in on the order of milliseconds in the preferred embodiment of the invention, such that the pressure signal is constantly being corrected for accuracy's sake.

The loop including blocks 120, 122, and 124 is entered only upon a change of state of the coils, that is, upon resetting the timer at 120. If a microprocessor operating according to the flowchart of FIG. 7 is used to control both of the coils, the timer is reset alternately at 12 and 22 seconds intervals, and the "on" and "off" states of the relays vary accordingly. If the coils were separately controlled the reset signal would cause them to be on for 46 seconds, and to then be off for 22 seconds. In either event the flow rate only needs to be checked on the order of once or twice per minute as indicated; in typical liquid chromatography experiments the flow rate changes only very slowly, over periods on the order of hours. The remainder of the processing steps shown in FIG. 7, i.e. steps 126-134 which control power in accordance with comparison of the pressure signal to the corresponding setpoint, are performed much more frequently.

The quantity D is indicative as mentioned above of the amount of the total available power which is actually supplied to the coils. The manner in which this is accomplished will now be described.

In the preferred embodiment of the invention, the power supplied to the coils is AC power provided by a transformer coupled to the usual 120 VAC power lines. The transformer secondary supplies power at 30 VAC corresponding to the 2 ohm resistance of typical coils 14. The actual amount of power supplied is determined by simply applying the 60 hz AC waveform, or not, as required, under the control of the relays. In a successfully tested embodiment of the invention involving microprocessor control programmed as indicated in connection with FIG. 7, zero-crossing relays are used, such that only whole half-cycles of the power waveform are supplied to the coil.

Figure 8:
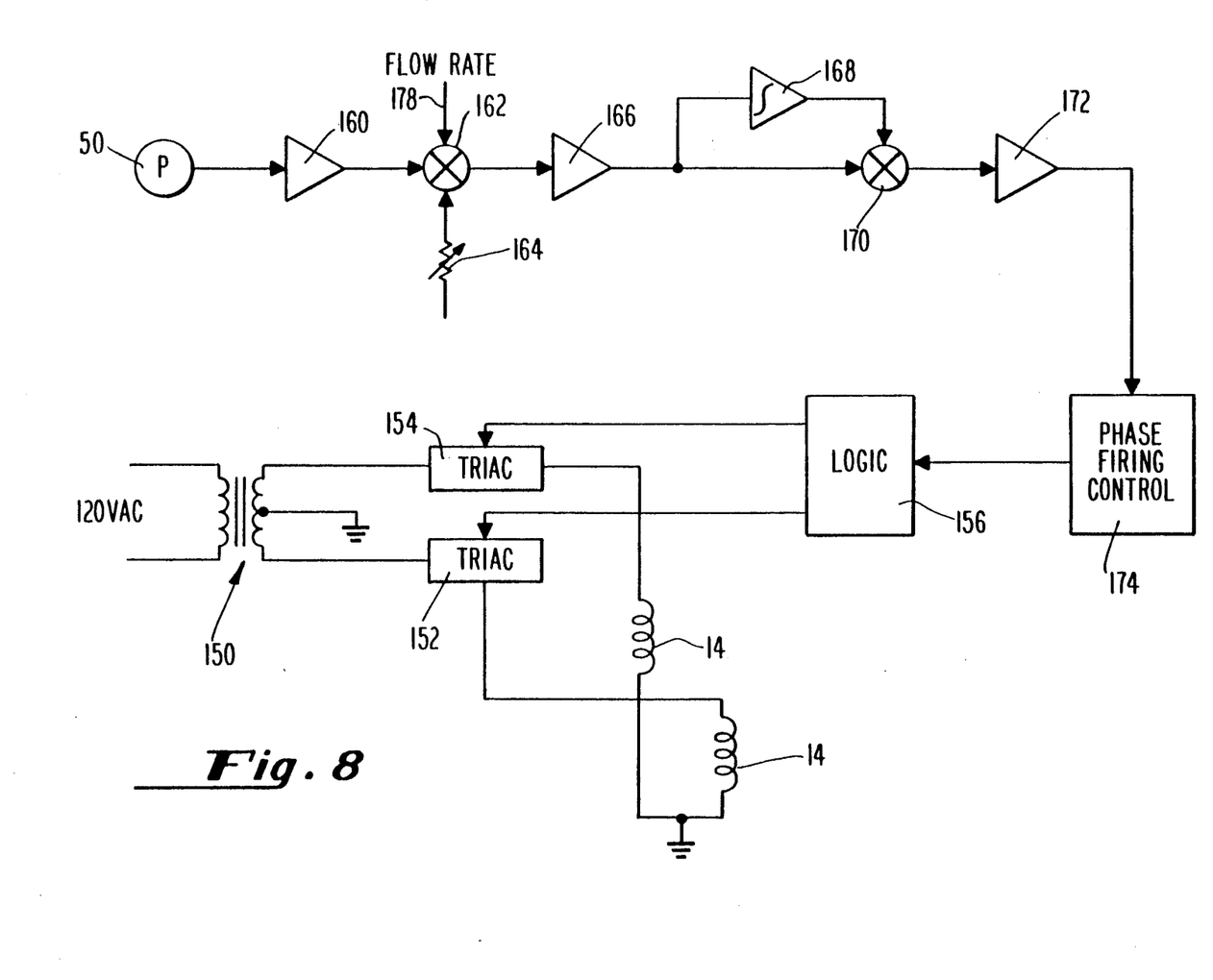
FIG. 8 shows in block diagram form an analog circuit for controlling the pump according to the invention.

FIG. 8 shows a circuit in which a number of the functions of the microprocessor-based controller described in connection with the flowchart of FIG. 7 are essentially replaced by analog circuit elements. FIG. 8 also shows the power supply circuitry, which is generally similar in both analog and microprocessor embodiments of the invention. The power circuit comprises a transformer 150 connected to the 120 VAC power line. Transformer 150 is center-tapped, and the end taps are provided to triacs 152 and 154, which are connected respectively to the heating coils 14 (FIG. 3), 30 (FIG. 4). The triacs 152 and 154 are functionally different than the solid state relays described above in connection with FIG. 7, in that the embodiment of FIG. 8 utilizes pulse width modulation for power control, rather than zero crossing firing. The actual amount of power supplied is determined by the position of the triac gate firing pulses with respect to time, synchronized with zero crossings of the 60 Hz. line frequency. Thus pulses delayed by longer periods of time with respect to the zero-crossings allow power to be developed in the coils for a smaller fraction of each half wave of transformer secondary voltage. Conversely, very short pulse delays equate to maximum power supplied to the coils. By comparison, and as mentioned above the microprocessor based controller supplies only whole half-waves of the power from the transformer secondary.

The signal from pressure transducer 50 is amplified at 160 and compared in a summing junction 162 with both a setpoint signal, provided as indicated schematically by a potentionmeter 164, and the flow rate signal 178. The signal is again amplified at 166 and is integrated at 168. The integrated signal and the amplified signal are summing in a second summing junction 170, such that a control signal is present at the output of summing junction 170 even if the setpoint, pressure transducer and flow rate signals are equal. The output from summing junction 170, amplified at 172, is then supplied to the phase firing control network 174 which provides control input to the triacs as directed by logic circuitry 156. The logic network 156 operates to properly gate the phase priate periods to produce the 46/22 second on/off intervals used in the preferred embodiment of the invention.

As will be appreciated by those skilled in the art, in this embodiment as well as in the microprocessor-implemented embodiment discussed in connection with FIG. 7, the signal from the pressure transducer 50 directly controls the amount of heat generated in the coils 14, which in turn controls the pressure, such that a complete control circuit including feedback is provided. In the embodiment shown, the flow signal is also used for control, by providing the flow rate signal as an input to summing junction 162, as shown at 178.

Figure 9:
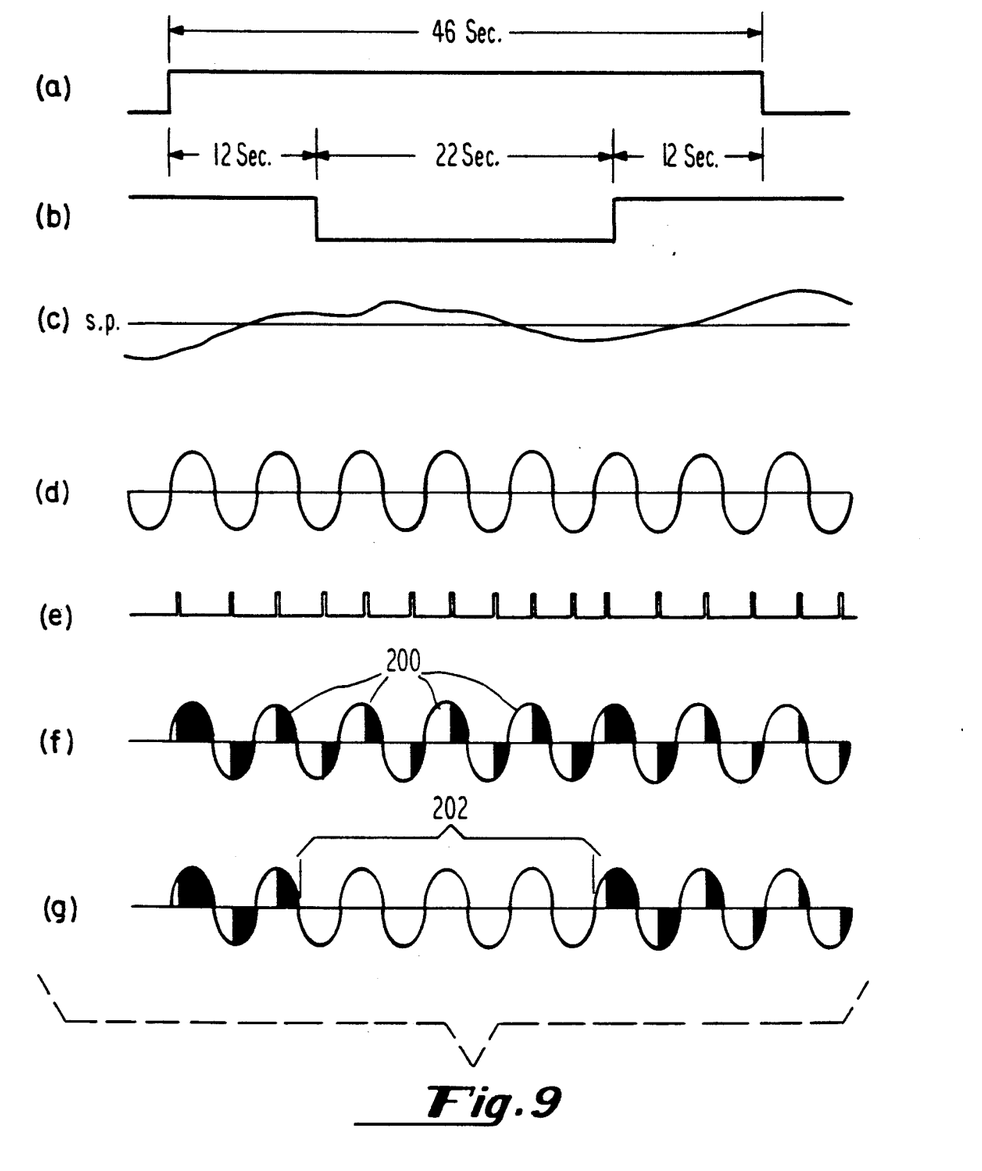

FIG. 9 shows the supply of power to coils 14 (FIG. 3), 30 (FIG. 4) for the "analog" embodiment of FIG. 8. FIG. 9a shows the period during which coil 1 is "on", indicating the 46-second "on" period; the corresponding "off" period is 22 seconds long. Coil 2 is similarly "on" for 46 seconds and "off" for 22, but its "off" period is centered with respect to the 46 second "on" period of coil 1, as shown in FIG. 9b, such that there are periods of 12 seconds before and after each "off" period during which both coils are "on". A typical AC power waveform is shown in FIG. 9d and is uniform throughout FIG. 9c represents an exemplary variation of the control signal from amplifier 172 about a nominal setpoint FIG. 9e shows the pulses output by the phase firing circuit 174; the displacement of these pulses in time from the zero crossings of the line frequency of FIG. 9d correspond to the deviation of the control signal from the setpoint. FIG. 9f shows the power which is supplied to coil 1, corresponding to the spacing of the pulses of FIG. 9e from the zero-crossings. The darkened areas of FIG. 9f represent the period of time in each half cycle of the line voltage during which the coil is activated. It can be seen that the "on" time is proportional to the amplitude of the control signal 9c with respect to the nominal setpoint. Power is supplied to the coil even when the pressure is greater than the setpoint, as indicated generally at 200. FIG. 9g shows the power signal for coil 2; as indicated, no power is supplied at during period 202, corresponding to the 22-sec. "off" period.

Figure 10:
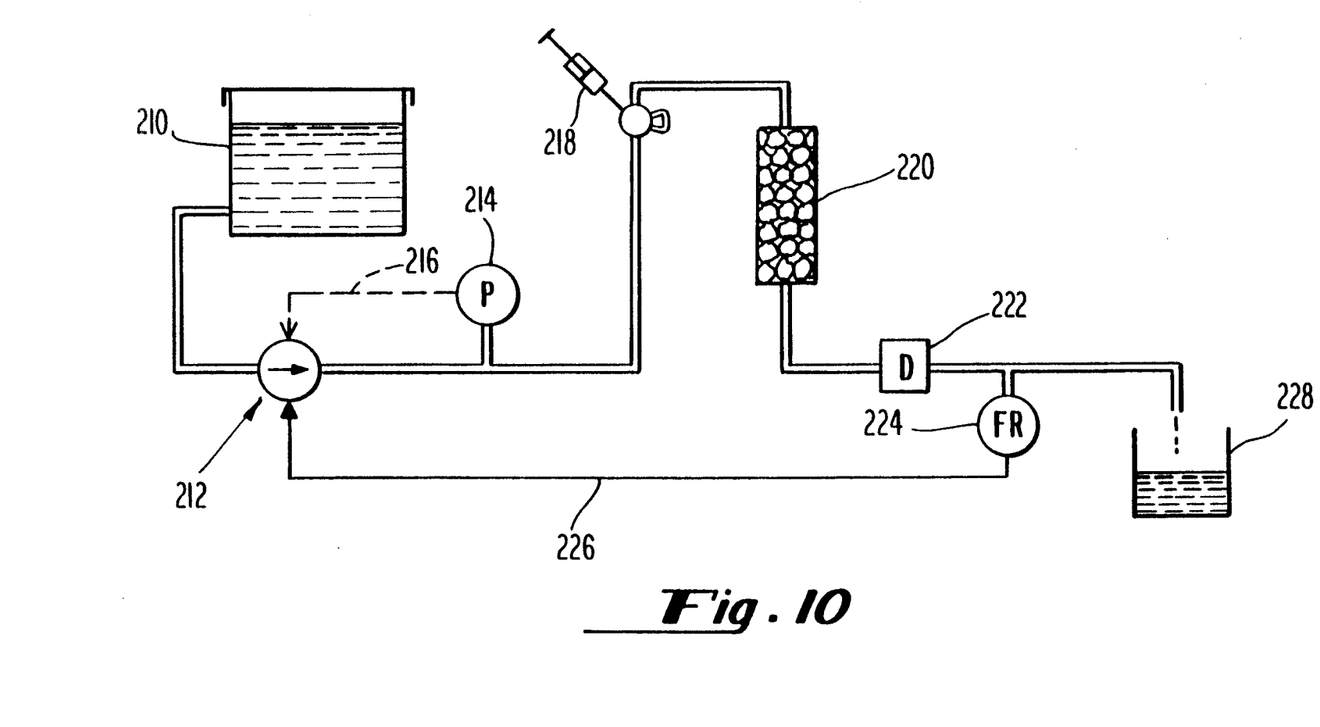
FIG. 10 shows a schematic view of a exemplary chromatographic system according to the present invention.

FIG. 10 shows a schematic view of a chromatographic system including the pump of the invention. A reservoir of solvent 210 is connected by a pipe to the pump of the invention indicated generally at 212. Any one of the embodiments of the pump discussed above can be employed as pump 212, specifically including the "dual pump" embodiments described in connection with FIGS. 3 and 4. If a pressure feedback signal is desired, a pressure signal developed by a pressure transducer 214 is fed back to the pump 212 as indicated in phantom at 216. A sample injection port is provided, as indicated by an injection septum 218. The solvent/sample combination is then supplied to a typical liquid chromatography column 220 which may comprise a chamber filled with any of a wide variety of materials known in the art to be useful in liquid chromatographic applications. The sample concentration in the eluted fluid is detected by a detector 222. The flow rate of the eluted fluid is measured by the time-of-flight flow meter 224 as discussed generally above, and the flow rate signal is fed back as indicated at 226 for control of the pump 212 again as discussed above. Finally the sample is sent through a drain indicated at 228. A wide variety of possible liquid chromatographic systems are intended to be embraced by the exemplary showing of FIG. 10, and the invention claimed herein is not to be limited by the type of liquid chromatographic system with which the pump of the invention is to be used.

It will be appreciated by those skilled in the art that there has been described an improved pump suitable for high pressure applications such as liquid chromatography. The pump of the invention has been described in several preferred embodiments suitable for a wide variety of operating conditions The only moving parts in the pump of the invention are check valves, which are reliably self-actuated, and the operation of which is not nearly as critical mechanically as is the operation of a piston sliding within a cylinder Of course it will be realized by those of skill in the art that the check valves could readily be replaced with solenoid valves controlled by the controller device. The fact that feedback of pressure and/or flow rate is provided to the controller allows essentially unlimited and extremely subtle control of pressure and flow, while completely avoiding adjustment of mechanical linkages and the like which can be troublesome in mechanical pumps. Control may be accomplished by simple and well understood expedients such as pulse width modulation of an electrical power signal; this allows significant versatility in flow control, together with great ease and flexibility of use.

Those of skill in the art will also recognize that the ultimate pressure obtained by the pump of the invention is dependent on the average temperature differential realized between the "hot" and "cool" conditions of the heated fluid, whether this is the fluid to be pumped itself, or is a separate working fluid, as in the embodiment of FIGS. 2 and 4. The rate of temperature variation has to do only with the length of the on and off portions of the duty cycle, and hence is relevant to the maximum flow rate provided by the pump of the invention. It is well within the skill of the art to increase the rate of heating and cooling, so as to increase the flow rate capabilities of the pump of the invention. Similarly, it is within the skill of the art to multiply the individual pump assemblies, further increasing maximum flow rate.

It will also be appreciated by those skilled in the art that the pumping chamber, whether one chamber of a diaphragm cell as in the embodiment of FIGS. 2 and 4, or a directly-heated length of tubing (FIGS. 1 and 3), need not be connected such that all fluid passing between the inlet and outlet check valves passes through the pumping chamber. In an entirely equivalent arrangement the chamber is a "branch" off the line directly connecting these check valves, as shown in the Bowen et al. and Van Hise patents discussed above.

Finally, it will be appreciated that while this application speaks in terms of a pump for fluids, it is equally applicable to the pumping of substances which are gaseous at ordinary temperatures and pressures, and the appended claims should be so construed.

It will be therefore understood that while a preferred embodiment of the invention has been described, a number of modifications and improvements thereto are possible without departure from the spirit and scope of the invention, which is therefore not to be limited by the above exemplary disclosure, but only by the following claims.

We claim:

1. A pump for liquids capable of generating high pressure and controlled flow rate comprising:
    a chamber having a first valve means and a second valve means, said chamber and valve means being adapted to repetitively expel pressurized liquid from the chamber through the second valve means responsive to heating the liquid and to repetitively refill the chamber with liquid through the first valve means;
    means for repetitively heating liquid within said chamber to intermittently expel pressurized liquid therefrom upon opening of the second valve means;
    means to measure the pressure and flow rate of the liquid; and
    controller means to control the amount of heating of said liquid in relation to the measured pressure and flow rate of the liquid in order to provide a controllable flow rate of liquid from the pump.

2. The pump of claim 1, wherein the amount of heat imparted to said chamber is controlled by modulation of a power wave form applied to said chamber by said controller means.

3. The pump of claim 2, wherein said modulation is pulse width modulation.

4. The pump of claim 3, wherein said pulse width modulation is synchronized to an AC power waveform supplied to said means for heating said tubing.

5. The pump of claim 1, wherein said chamber comprises a length of tubing, and said valve means comprise first and second check valves.

6. The pump of claim 1, wherein plural said lengths of tubing and first and second check valves are provided, said first check valves being connected to a common source of fluid to be pumped and said second check valves being connected in common to said means for measuring the pressure and/or flow rate, said controller means comprising means for supplying heat alternately to said plural sections of tubing, whereby a substantially uniform net flow rate is provided.

7. The pump of claim 1, wherein said controller means comprises means for receiving setpoint information relative to desired liquid pressure and flow rate, means for comparison of said setpoint information to measured values for pressure and flow rate, and means for controlling the amount of heat supplied to said means for heating said chamber in response to said comparison.

8. A pump for liquid chromatographic applications, comprising:
    controller means, and
    first and second pumping devices, each of said pumping devices comprising:
    a first check valve;
    a second check valve; and
    pump means connected between said first and second check valves, and adapted to urge fluid out said second check valve upon application of heat thereto;
    said first check valves being connected to a source of fluid to be pumped;
    said second check valves being connected to one another and to a point of use of said fluid to be pumped,
    said first and second pumping means being alternately energized by said controller means to pump fluid out the corresponding second check valves, said pumps being operated by said controller means in accordance with predetermined duty cycles established such that each one of said pumps is operated during an "on" portion of its duty cycle and is not operated during an "off" portion of its duty cycle, said duty cycles being arranged with respect to one another such that at least one of said pumps is in operation at all times and both of said pumps are in operation at certain other times, and
    wherein a first one of said second check valves connected to a first one of said pump means only opens when the other of said pump means has ceased operations at the end of an "on" portion of its duty cycle, and wherein the second one of said second check valves closes only when the pressure in a line connecting said second check valves is substantially equal to the pressure exerted by said first one of said pumping means, and vice versa, whereby the pressure in the line connecting said second check valves and said point of use is maintained substantially constant, and wherein said first and second pump means each comprise a container adapted to contain a volume of said fluid to be pumped, and means for heating said container, and wherein said container comprises a length of electrically resistive tubing adapted to be heated by resistance heating upon application of an electric current thereto.

9. The pump of claim 8 wherein said controller means is adapted to control the amount of heating of each of said lengths of tubing by modulation of the power supplied thereto during the "on" portion of the duty cycle thereof.

10. The pump of claim 9 wherein said modulation is pulse-width modulation.

11. A pump suitable for liquid chromatographic applications comprising:
   (a) controller means; and
   (b) first and second pumping devices, each of said pumping devices comprising:
   a first check valve;
   a second check valve; and
   pump means connected between said first and second check valves, and adapted to urge fluid out said second check valve upon application of heat thereto;
   each of said first check valves being connected to a fluid to be pumped;
   each of said second check valves being connected to a point of use of said fluid to be pumped;
   said first and second pumping means being alternately energized by said controller means to pump fluid out the corresponding second check valves, said pumps being operated by said controller means in accordance with predetermined duty cycles established such that each one of said pumps is operated during an "on" portion of its duty cycle and is not operated during an "off" portion of its duty cycle, said duty cycles being arranged with respect to one another such that at least one of said pumps is in operation at all times and both of said pumps are in operation at certain other times;

wherein a first one of said second check valves connected to a first one of said pump means only opens when the other of said pump means has ceased operations at the end of an "on" portion of its duty cycle, and wherein the second one of said second check valves closes only when the pressure in a line connecting said second check valves is substantially equal to the pressure exerted by said first one of said pumping means, and vice versa, whereby the pressure in the line connecting said second check valves and said point of use is maintained substantially constant;

wherein each of said pump means comprises a diaphragm cell defining first and second diaphragm chambers separated by flexible diaphragm means, said first and second check valves of said pumping device being connected to the first one of said chambers, said second chamber being connected to means for containing a volume of working fluid adapted to be heated to deflect said diaphragm means in order to urge fluid in said first chamber through said second check valve, and wherein said means for containing a volume of working fluid comprises a length of tubing formed of an electrically resistive material adapted to be heated by passage of an electric current therethrough.

12. The pump of claim 11 wherein said controller means controls the amount of power supplied to said tubing for heating of said working fluid.

13. The pump of claim 12 wherein said controller means controls the power supplied to said tubing by modulation of a power wave form supplied to said pump means during said "on" portion of said duty cycle.

14. The pump of claim 13 wherein said modulation is pulse width modulation.

* * * * *